United States Patent
Maglaras et al.

(10) Patent No.: US 10,660,764 B2
(45) Date of Patent: May 26, 2020

(54) LOAD SUSTAINING BONE SCAFFOLDS FOR SPINAL FUSION UTILIZING HYPERBOLIC STRUTS AND TRANSLATIONAL STRENGTH GRADIENTS

(71) Applicant: THE TRUSTEES OF THE STEVENS INSTITUTE OF TECHNOLOGY, Hoboken, NJ (US)

(72) Inventors: Constance Maglaras, Flushing, NY (US); Antonio Valdevit, Effort, PA (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 316 days.

(21) Appl. No.: 15/621,698

(22) Filed: Jun. 13, 2017

(65) Prior Publication Data
US 2017/0354513 A1 Dec. 14, 2017

Related U.S. Application Data

(60) Provisional application No. 62/349,915, filed on Jun. 14, 2016.

(51) Int. Cl.
*A61F 2/44* (2006.01)
*A61F 2/30* (2006.01)

(52) U.S. Cl.
CPC .......... *A61F 2/4455* (2013.01); *A61F 2/4465* (2013.01); *A61F 2002/30985* (2013.01); *A61F 2002/4495* (2013.01)

(58) Field of Classification Search
CPC .......... A61F 2/44; A61F 2/4455; A61F 2/446; A61F 2/4465; A61F 2/447; A61F 2002/4475; A61F 2002/4495
See application file for complete search history.

(56) References Cited

U.S. PATENT DOCUMENTS

| | | | |
|---|---|---|---|
| 4,820,305 A | 4/1989 | Harms et al. | |
| 5,282,861 A * | 2/1994 | Kaplan | A61F 2/28 623/23.51 |
| 6,206,924 B1 * | 3/2001 | Timm | A61F 2/28 623/17.11 |
| 6,228,123 B1 | 5/2001 | Dezzani | |
| 6,520,996 B1 * | 2/2003 | Manasas | B22F 3/1055 623/23.5 |

(Continued)

*Primary Examiner* — Eric S Gibson
(74) *Attorney, Agent, or Firm* — Greenberg Traurig, LLP

(57) ABSTRACT

A spinal fusion bone scaffold having a first member including a first base plate and a first plurality of struts each having a first end engaging the first base plate and a second, free end. The first plurality of struts is configured to form at least part of a hyperbolic curve such that said bone scaffold includes an overall optimized hyperboloid shape having an outer diameter and an inner waist diameter. The scaffold may include a second member including a second plurality of struts each having a first end and a second end, each of the second plurality of struts being configured to form at least part of the hyperbolic curve. The scaffold includes connecting means for connecting said second member to said first member, which are aligned so as to complete the hyperbolic curve while generating hyperboloid geometry of the bone scaffold.

12 Claims, 11 Drawing Sheets

(56) References Cited

U.S. PATENT DOCUMENTS

| | | | |
|---|---|---|---|
| 6,931,812 B1* | 8/2005 | Lipscomb | E04B 1/19 |
| | | | 52/648.1 |
| 7,628,814 B2* | 12/2009 | Studer | A61F 2/4425 |
| | | | 623/17.11 |
| 8,430,930 B2* | 4/2013 | Hunt | A61F 2/28 |
| | | | 623/17.11 |
| 8,530,560 B2* | 9/2013 | Kerr | A61N 1/3622 |
| | | | 424/490 |
| 8,623,090 B2* | 1/2014 | Butler | A61F 2/442 |
| | | | 623/17.15 |
| 8,702,808 B2 | 4/2014 | Teoh et al. | |
| 8,826,602 B1 | 9/2014 | Lipscomb | |
| 9,039,766 B1* | 5/2015 | Fonte | A61F 2/442 |
| | | | 623/17.11 |
| 9,271,845 B2* | 3/2016 | Hunt | A61F 2/4455 |
| 9,308,297 B2* | 4/2016 | Kerr | A61N 1/3622 |
| 9,918,849 B2* | 3/2018 | Morris | A61F 2/30744 |
| 10,064,726 B1* | 9/2018 | Wei | A61F 2/30942 |
| 2005/0027364 A1* | 2/2005 | Kim | A61F 2/4425 |
| | | | 623/17.13 |
| 2005/0112397 A1* | 5/2005 | Rolfe | A61B 17/8605 |
| | | | 428/593 |
| 2006/0052872 A1* | 3/2006 | Studer | A61F 2/4425 |
| | | | 623/17.13 |
| 2006/0100706 A1* | 5/2006 | Shadduck | A61B 17/1617 |
| | | | 623/17.11 |
| 2006/0293749 A1* | 12/2006 | Hudgins | A61F 2/441 |
| | | | 623/17.11 |
| 2007/0219634 A1* | 9/2007 | Greenhalgh | A61F 2/446 |
| | | | 623/17.16 |
| 2008/0077244 A1* | 3/2008 | Robinson | A61F 2/442 |
| | | | 623/17.16 |
| 2008/0206297 A1* | 8/2008 | Roeder | A61F 2/28 |
| | | | 424/422 |
| 2009/0149958 A1* | 6/2009 | Prewett | A61F 2/442 |
| | | | 623/17.16 |
| 2010/0137990 A1* | 6/2010 | Apatsidis | A61B 17/866 |
| | | | 623/17.16 |
| 2010/0298950 A1* | 11/2010 | McDonnell | A61F 2/30771 |
| | | | 623/23.53 |
| 2011/0022180 A1* | 1/2011 | Melkent | A61L 27/425 |
| | | | 623/23.5 |
| 2011/0045087 A1* | 2/2011 | Kerr | A61N 1/3622 |
| | | | 424/490 |
| 2011/0313532 A1* | 12/2011 | Hunt | A61F 2/30767 |
| | | | 623/18.11 |
| 2012/0150299 A1 | 6/2012 | Ergun et al. | |
| 2013/0116793 A1* | 5/2013 | Kloss | A61F 2/442 |
| | | | 623/17.16 |
| 2013/0123935 A1* | 5/2013 | Hunt | A61F 2/28 |
| | | | 623/23.61 |
| 2013/0184826 A1* | 7/2013 | Thaiyananthan | A61F 2/442 |
| | | | 623/17.16 |
| 2014/0121776 A1* | 5/2014 | Hunt | A61F 2/4455 |
| | | | 623/17.16 |
| 2014/0288649 A1* | 9/2014 | Hunt | A61F 2/447 |
| | | | 623/16.11 |
| 2014/0288650 A1* | 9/2014 | Hunt | A61F 2/447 |
| | | | 623/16.11 |
| 2015/0127106 A1* | 5/2015 | Partee | A61L 27/365 |
| | | | 623/17.11 |
| 2015/0150681 A1 | 6/2015 | Ricci et al. | |
| 2016/0324656 A1* | 11/2016 | Morris | A61F 2/30744 |
| 2017/0258606 A1* | 9/2017 | Afzal | A61F 2/4465 |
| 2017/0354513 A1* | 12/2017 | Maglaras | A61F 2/4455 |
| 2018/0296343 A1* | 10/2018 | Wei | B33Y 10/00 |
| 2018/0303616 A1* | 10/2018 | Bhattacharyya | A61F 2/30942 |
| 2018/0368981 A1* | 12/2018 | Mattes | A61L 27/045 |
| 2019/0000636 A1* | 1/2019 | Kim | B33Y 80/00 |
| 2019/0099515 A1* | 4/2019 | Bagga | A61L 27/10 |
| 2019/0133783 A1* | 5/2019 | Unger | A61F 2/30771 |

* cited by examiner

LOAD SUSTAINING BONE SCAFFOLDS FOR SPINAL FUSION UTILIZING HYPERBOLIC STRUTS AND TRANSLATIONAL STRENGTH GRADIENTS

RELATED APPLICATION

This is a Section 111(a) application relating to and claiming the benefit of U.S. Provisional Patent Application No. 62/349,915, filed Jun. 14, 2016, the disclosure of which is incorporated by reference in its entirety herein.

FIELD OF INVENTION

The present invention relates to biomedical devices, and more particularly, to bone scaffolds and implants.

BACKGROUND

Improvements to bone fusion employing biologically active and biomechanically stable scaffolds remain a challenge. While cells are proliferated using scaffolds, the lack of mechanical integrity, retainment of biological material and geometry associated with known scaffolds are undesirable in the spine. In spinal fusion applications, stability is achieved through the use of non-biodegradable cages. Fusion cages are typically made from metals such as titanium or cobalt chromium alloys, or from polyetheretherketone (PEEK). These implants have mechanical properties that are much greater than the mechanical properties of bone, and can cause implant subsidence, stress shielding and movement. Physiological loading in the spine is characterized as coupled loading, in that tensile, shear, torsional, bending, and compressive forces are experienced in conjunction with one another. The intrinsic hyperbolic geometry of the vertebral body allows for such coupled motion. There are several problems with current methods for interbody fusion. Traditional fusion cages are rigid (typically made from metal or PEEK) and do not allow for natural load transfer within the spine. Current fusion devices do not permit load sharing between the implant and the graft contained therein. These devices lack loading of the biological material contained therein, which is extremely problematic for bone. Bone will grow and/or resorb in response to external loading and constraints. Unless the graft is subjected to loading forces, the bone will resorb and fail. Autografting is the current "golden standard" in grafting for fusion and to treat bone defects during surgery. However, this can be traumatic for the patient as there is the risk of donor site morbidity, pain, nerve injury and resorption of the graft. Synthetic materials (used instead of autografts) have no biological activity, while cadaveric grafts (i.e., allografts) suffer from a limited supply.

SUMMARY

In view of the foregoing background, a surgically sized bone scaffold/implant is provided. The disclosed bone scaffold can sustain physiological loading and is suitable for cell and bone graft deposition to facilitate bone fusion in the spine. A main advantage of the invention is its increased mechanical properties and biologically active capability. The optimized hyperboloid geometry makes the scaffold an efficient load-bearing, high-strength, lightweight structure. One embodiment of the scaffold weighs approximately 4 grams and can sustain about 4900 N of compressive force. The interconnecting hyperbolic struts making up the hyperboloid enable compressive, bending, and torsional forces to be transmitted as axial (compressive/tensile) forces. This is especially advantageous in bone because bone is strongest when loaded in its axial direction. This gives the scaffold the advantage of being able to provide immediate mechanical stability after implantation. Enhanced mechanical properties also permit greater loading amplitudes/greater mechanical stimulation during the cell culturing phase in the bioreactor. Cell seeding plays a major role in establishing a local environment for cellular attachment and subsequent proliferation toward mineralization. Cell seeding conditions influence the number of cells that attach and uniformity of distribution of cells throughout the scaffold. These factors ultimately play a role in cell viability, proliferation and mineralization. This is advantageous because cells need mechanical stimulation to grow. The scaffold provides immediate mechanical stability and bioactivity upon implantation.

Also advantageous over all other bone tissue repair devices is the customizable properties. The mechanical properties of the scaffold can be customized by various means. The number of rings, as well as the distance between each ring can be tailored for individual applications. The number, orientation, and size of struts can also be tailored to generate desired mechanical properties. The rings, as well as individual struts, can be made into any shape or orientation. As the scaffold is 3D printed, the design can be customized in computer aided design for patient specificity. The arrangement of struts can be customized to permit translational strength changes and porosities, a feature not found in current devices. Another main advantage of the scaffold is that it is completely bioresorbable. The scaffold can support physiological forces, regenerate bone tissue and degrade into harmless by-products in the body, thereby eliminating the use for metallic or non-biodegradable polymeric implants. Additionally, the invention permits a surgeon three surgical options to facilitate osteointegration; patient autograft, patient biopsy of mesenchymal stem cells, and synthetic or cadaveric graft. Another advantage over existing commercial implants is a reduced use of material for production and fabrication time, while sustaining physiological loading. Additionally, due to the design of the scaffold, a smaller portion of grafting material is necessary compared to similar sized spacers currently used in spinal fusion. The scaffold can also be used as a means for drug or osteoprogenitor delivery.

BRIEF DESCRIPTION OF THE DRAWINGS

For a more complete understanding of the present invention, reference is made to the following detailed description of an embodiment considered in conjunction with the accompanying drawings, in which.

DETAILED DESCRIPTION OF THE EXEMPLARY EMBODIMENT

Figure 1:
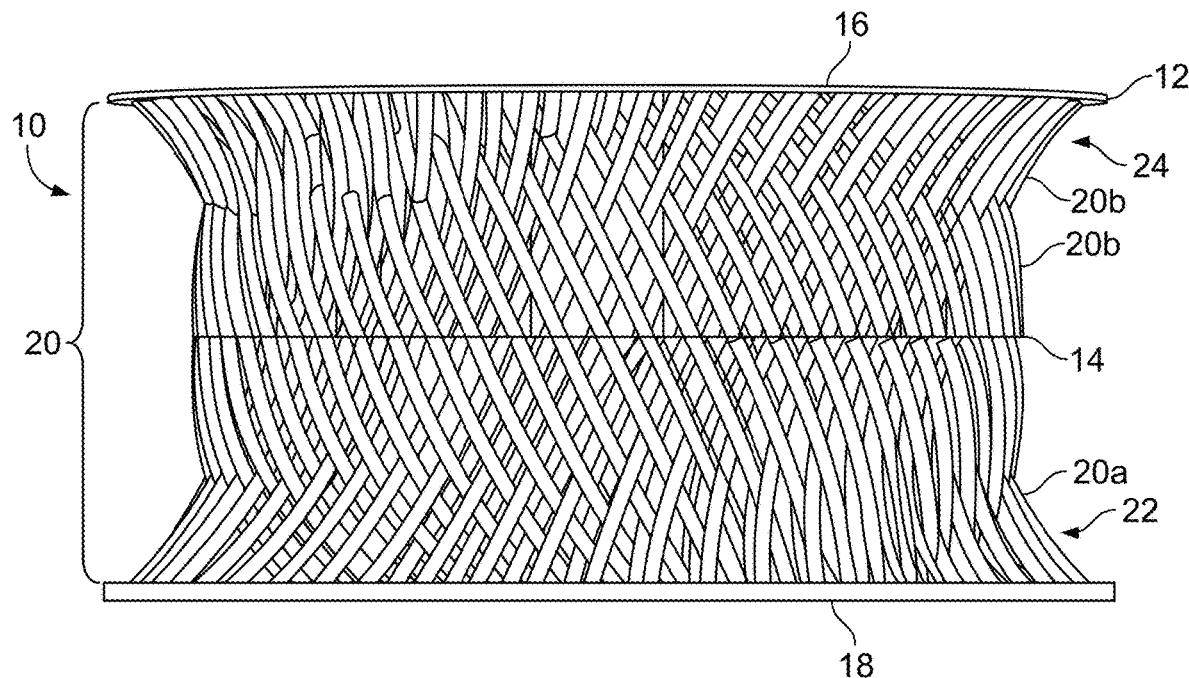
FIG. 1 is a side elevational view of a fully assembled bone scaffold according to a first embodiment of the present invention.

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

Detailed embodiments of the present invention are disclosed herein. It should be understood that the disclosed embodiments are merely illustrative of the invention that may be embodied in various forms. In addition, each of the examples given in connection with the various embodiments of the invention is intended to be illustrative, and not restrictive. Further, the Figures are not necessarily to scale, and some features may be exaggerated to show details of particular components. In addition, any measurements, specifications and the like shown in the Figures are intended to be illustrative, and not restrictive. Therefore, specific structural and functional details disclosed herein are not to be interpreted as limiting, but merely as examples for teaching one skilled in the art to variously employ the present invention.

All terms defined herein should be afforded their broadest possible interpretation, including any implied meanings as dictated by a reading of the specification as well as any words that a person having skill in the art and/or a dictionary, treatise, or similar authority would assign thereto.

Further, it should be noted that, as recited herein, the singular forms 'a,' "an," and "the" include the plural referents unless otherwise stated. Additionally, the terms "comprises" and "comprising" when used herein specify that certain features are present in that embodiment, however, this phrase should not be interpreted to preclude the presence or additional of additional steps, operations, features, components, and/or groups thereof.

The present disclosure generally relates to a surgically sized bone scaffold/implant that can sustain physiological loading and is suitable for cell and bone graft deposition to facilitate bone fusion in the spine. The bone scaffold of the present invention possesses increased mechanical properties and biologically active capability. The optimized hyperboloid geometry makes the scaffold an efficient load-bearing, high-strength, lightweight structure.

The scaffolds are designed using computer aided design. In the preferred embodiment, the scaffolds are fabricated via 3D printing technology (additive manufacturing) from polylactic acid (PLA) filament. PLA is a synthetic polymer used in bone tissue engineering as it is biocompatible and bioresorbable. PLA degrades over the course of one year; approximately the same amount of time for full spinal fusion to occur. Although 3D printing is the preferred method of manufacturing, the scaffold could also be made through other techniques including, but not limited to, laser sintering, computer numerical control (CNC) milling, and extrusion.

In alternate embodiments, the scaffold is formed from one or more other biocompatible materials. Such materials include metals, including but not limited to, titanium and cobalt chrome; ceramics; and polymers, including but not limited to, polycaprolactone (PCL). The scaffold could also be made of a composition of materials, as well as biological materials.

FIG. 1 is a side view of the full assembly of a scaffold 10 according to an embodiment of the present invention. The scaffold 10 has an overall optimized hyperboloid structure including an outer diameter 12, and an inner waist diameter 14. In alternate embodiments of the invention, the dimensions of the outer diameter 12 and inner waist diameter 14 can be altered to any desired number, such that the ratio can be any real number greater than zero. The outer and inner diameters 12, 14 can also be altered to generate any phase angle β value, which may be calculated according to the following equation:

$$\text{Tan}\beta = \frac{\sqrt{R^2 - a^2}}{H}$$

wherein,
β=phase angle;
R=outer radius of hyperboloid;
a=inner waist radius of hyperboloid; and
H=half of the height of the hyperboloid.

The scaffold 10 includes an upper base plate 16 at one (i.e., top) end thereof, and a lower base plate 18 at an opposite (i.e., bottom) end thereof. The base plates 14, 16 contain a plurality of struts 20 between them, as further discussed below.

Figure 2:
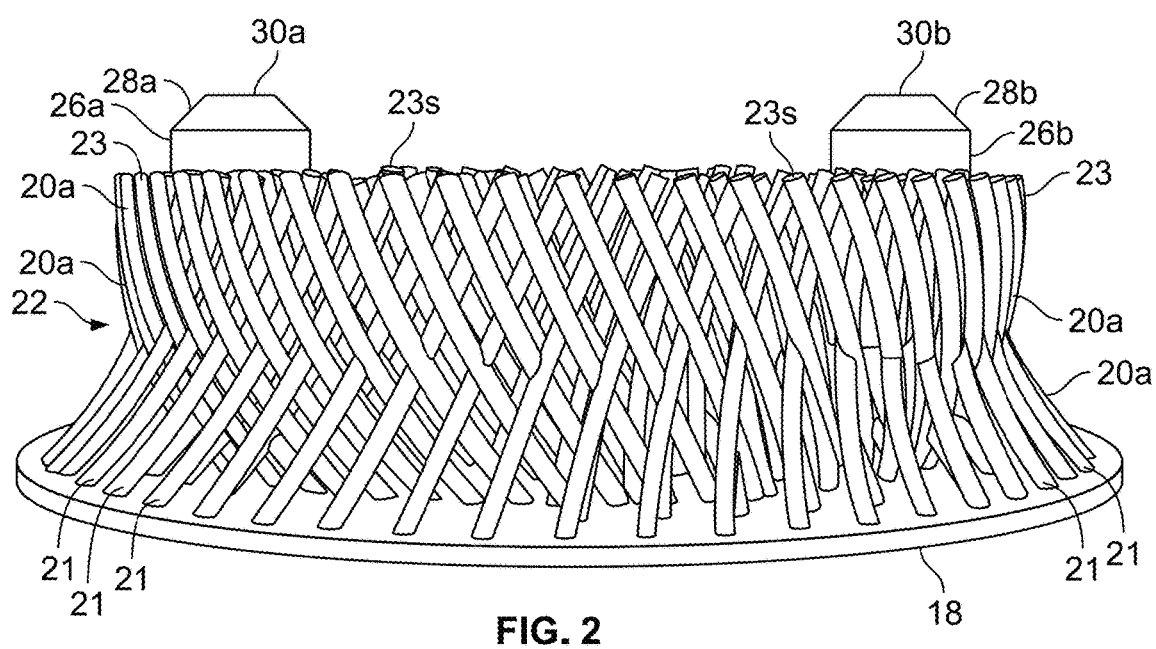
FIG. 2 is a side elevational view of a male member, or half, of the scaffold shown in FIG. 1.
Figure 3:
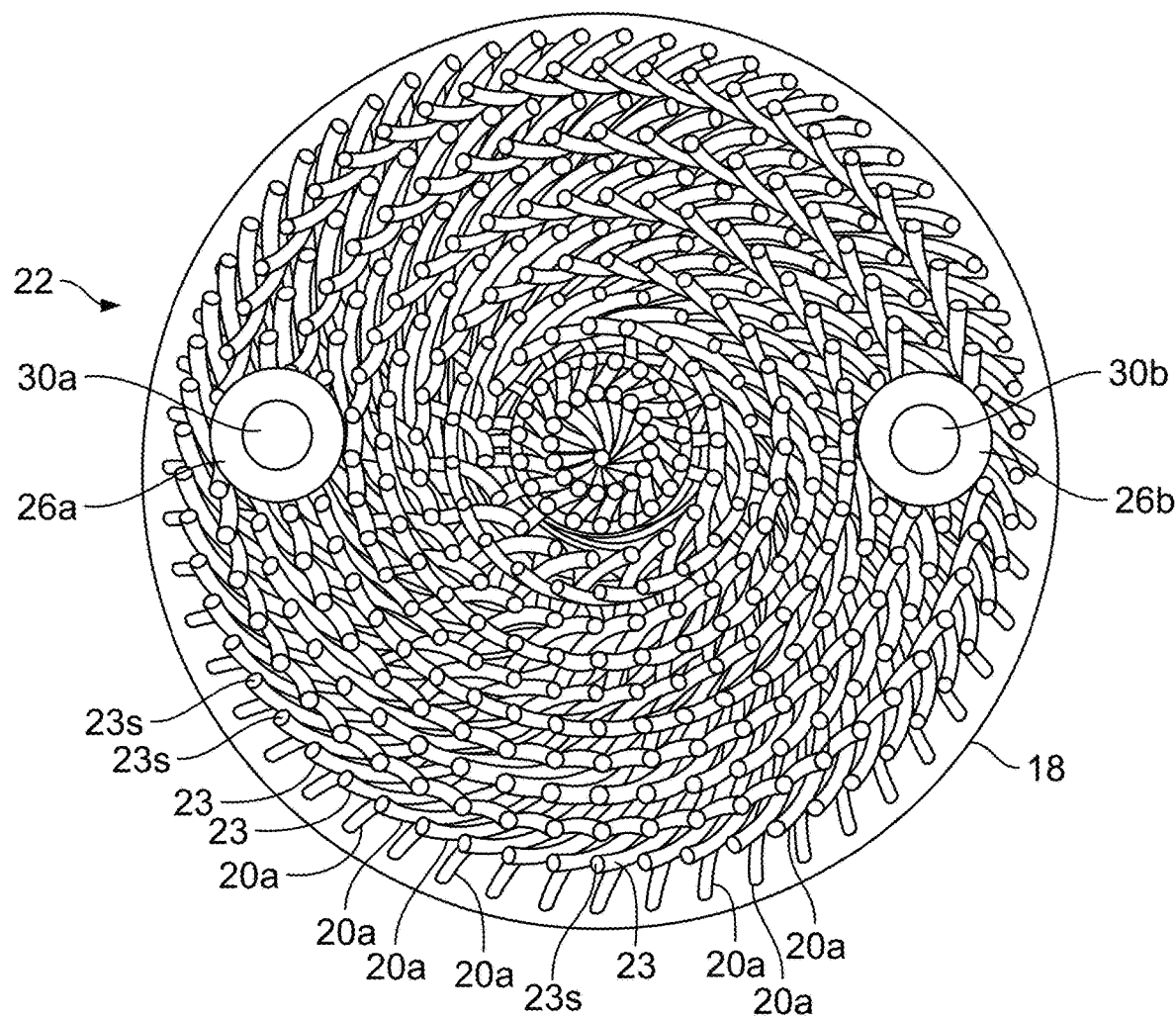
FIG. 3 is a top plan view of the male member shown in FIG. 2.
Figure 4:
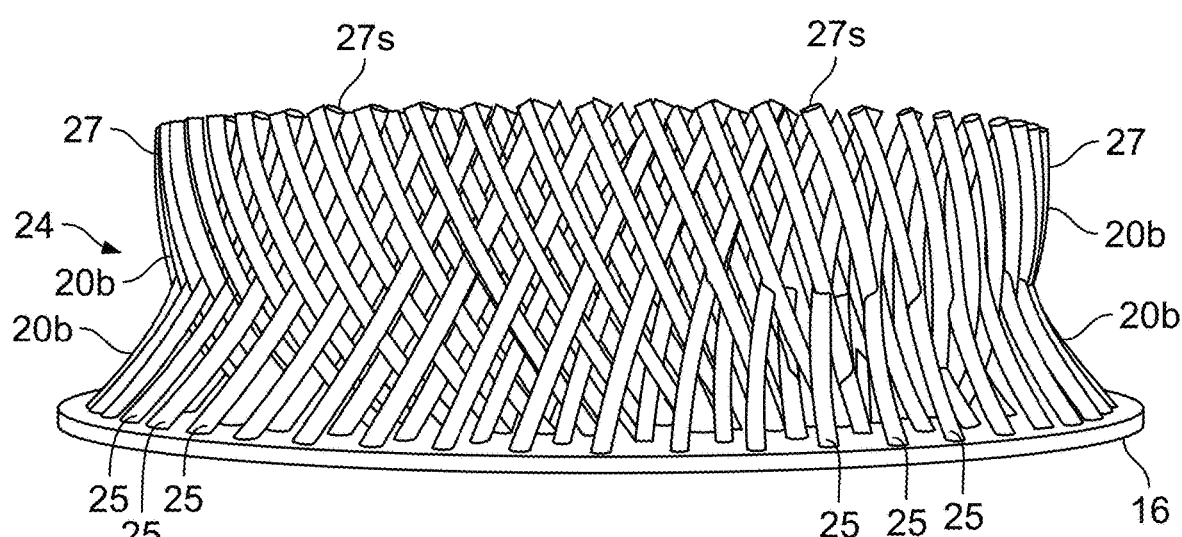
FIG. 4 is a side elevational view of a female member, or half, of the scaffold shown in FIG. 1.
Figure 5:
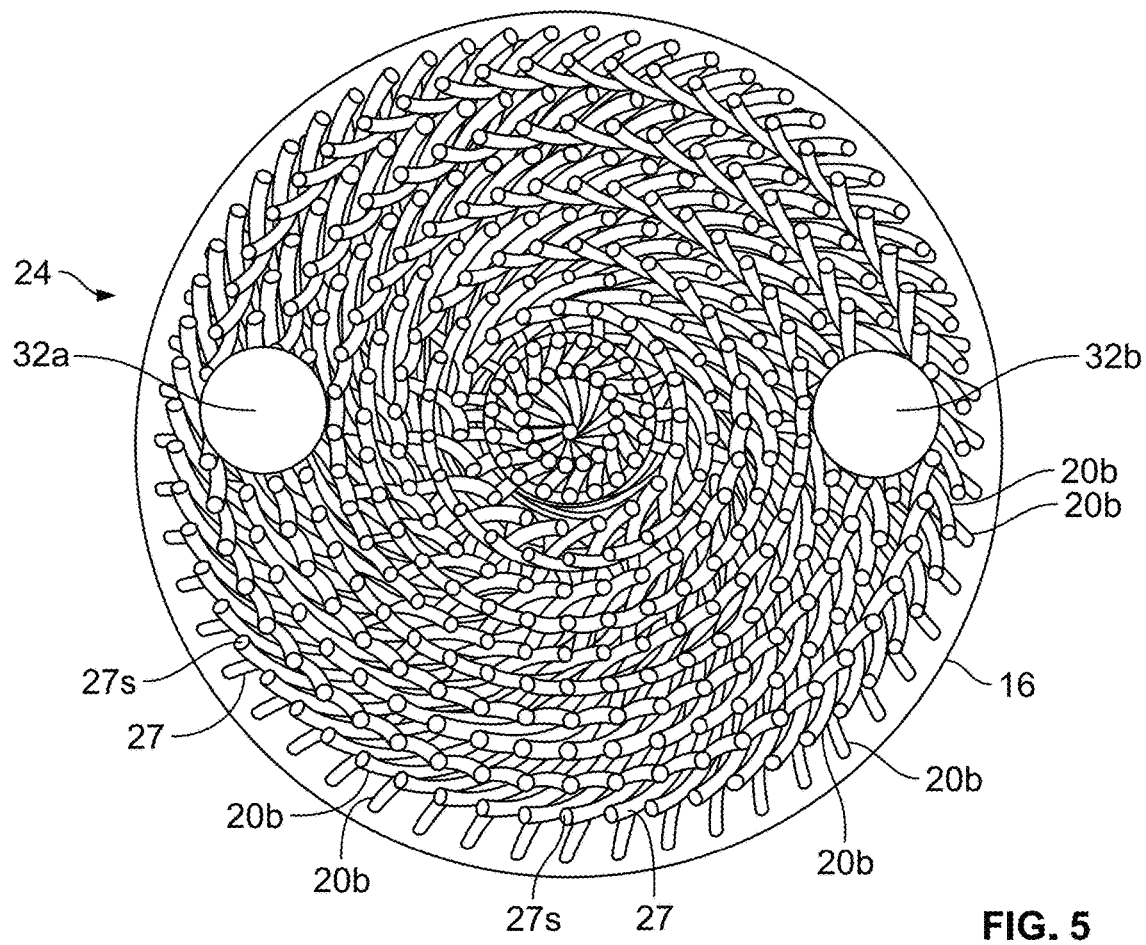
FIG. 5 is a top plan view of the female member shown in FIG. 4.

Referring now to FIGS. 2-5, the scaffold 10 is composed of two separate halves, or members, 22, 24. FIGS. 2 and 3 depict the male member 22, and FIGS. 4 and 5 depict the female member 24. The male member 22 and female member 24 are assembled and secured together to create a hyperboloid structure, as further discussed below.

As shown in FIGS. 2 and 3, the male member 22 includes a plurality of male struts 20a, each of which has a first end 21 secured to the lower base plate 18 and a second end 23 that is opposite the first end 21. Unlike the first ends 21, the second ends 23 are free ends, each having an exposed end surface 23s. FIG. 2 also shows the intersection of the male struts 20a, while FIG. 3 shows the exposed end surfaces 23s and the spatial configuration of the male struts 20a.

With continued reference to FIGS. 2 and 3, the male member 22 also includes two vertical alignment posts 26a, 26b, each of which has a spherical cap 28a, 28b, respectively. While two vertical alignment posts are shown, any number of posts or alignment configurations may be used (e.g., one, three, or four posts). The vertical alignment posts 26a, 26b are solid and preferably cylindrical, and extend upwardly from the lower base plate 18. The vertical alignment posts 26a, 26b each have a height that is greater than the height of the surrounding male struts 20a. Each of the spherical caps 28a, 28b includes a top surface 30a, 30b, respectively, which are preferably flat. In alternate embodiments, the alignment posts 26a, 26b and their respective post caps 28a, 28b can be of any geometry, and have a primary function of properly aligning the male and female members 22, 24, as further discussed below.

With reference to FIGS. 4 and 5, the female member 24 includes a plurality of female struts 20b, each of which has a first end 25 secured to the upper base plate 16 and a second end 27 that is opposite the first end 25. Unlike the first ends 25, the second ends 27 are free ends, each having an exposed end surface 27s. FIG. 4 also shows the intersection of the female struts 20b, while FIG. 5 shows the exposed end surfaces 27s and the spatial configuration of the female struts 20b.

With continued reference to FIG. 5, the female member 24 also includes two cylindrical bores, or holes, 32a, 32b that extend from the upper base plate 16, and are formed and surrounded by the female struts 20b. The cylindrical bores 32a, 32b are dimensioned to insertably receive the alignment posts 26a, 26b, respectively, and thereby align and secure together the male and female members 22, 24 of the scaffold 10. In the preferred embodiment of the invention, the height (i.e., depth) of each of the cylindrical bores 32a, 32b is greater than or equal to the height of the alignment posts 26a, 26b.

The exposed end surfaces 27s of the female struts 20b align with the corresponding exposed end surface 23s surfaces of the male struts 20a when the male and female members 22, 24 are aligned and connected, as illustrated in FIG. 1, so as to complete a hyperbolic curve while generating overall hyperboloid geometry. As the hyperbolic struts 20 are designed in two halves, 22, 24, the alignment posts 26a, 26b and cylindrical bores 32a, 32b are positioned so as to ensure proper alignment of the exposed end surfaces 23s, 27s of the struts 20a, 20b, respectively.

The mechanical integrity of the preferred embodiment of the scaffold 10 was tested in static compression and revealed a scaffold average yield load of 1691±93 N at an average yield displacement of 1.91±−0.2 mm (see Example 1 below). The scaffold yield strain was calculated to be 11+/−1%. The energy dissipation or area under the curve was 0.87±−0.09 J. Scaffold stiffness was calculated to be 1959±267 N/mm.

A dynamic analysis of the scaffold 10 was also performed on regional areas of the scaffold 10, and revealed that the material properties change at different regional locations within the scaffold 10, and that the scaffold 10 has a dual phased rate of decay, similar to the response of bone when loaded dynamically (see Example 2 below).

Figure 6:
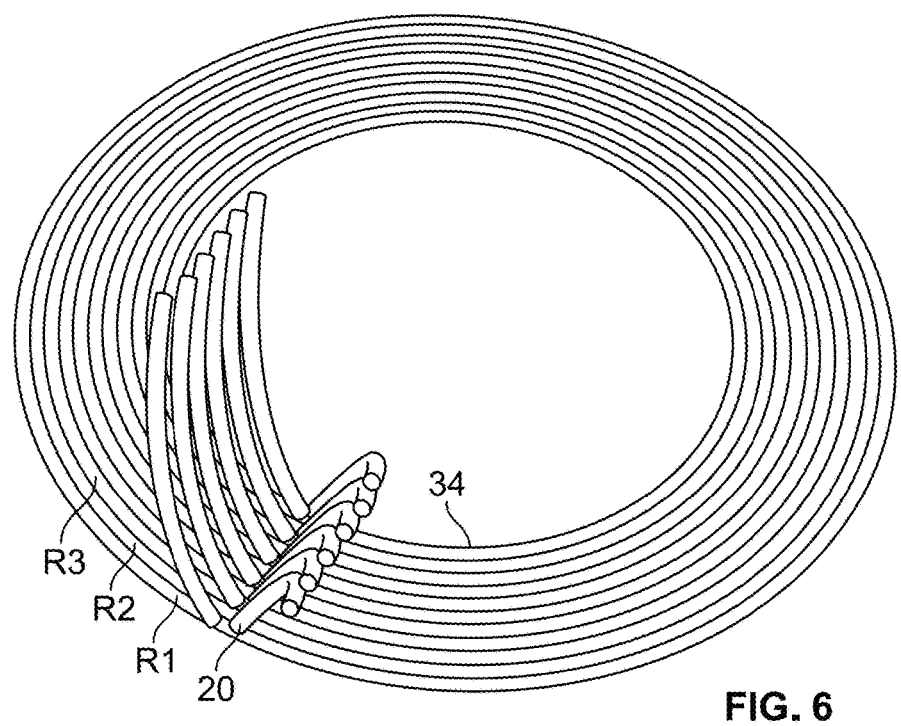
FIG. 6 is a schematic view of individual hyperbolic struts and the footprint of the concentric rings in which the hyperbolic struts are laid.
Figure 7:
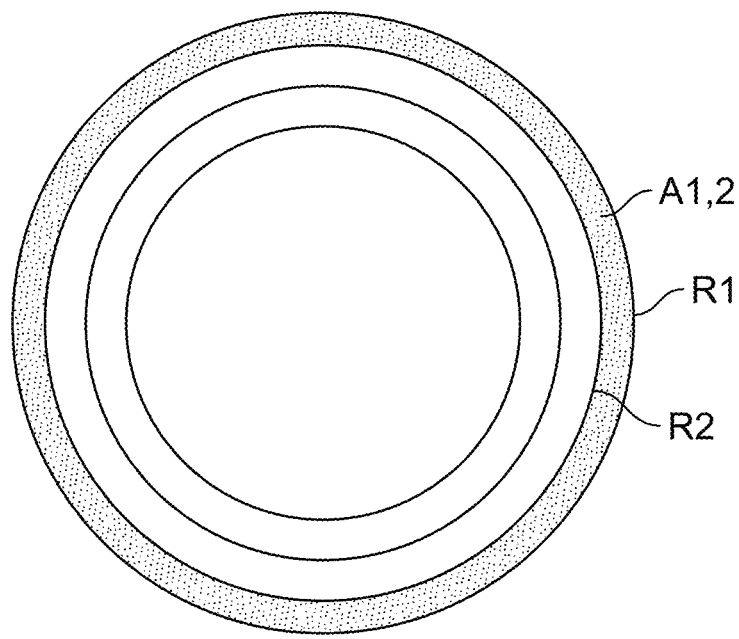
FIG. 7 is a schematic view of some of the concentric rings shown in FIG. 6.

The overall geometry of the scaffold 10 is a modeled optimized hyperboloid, which is formed by complex interconnections of the individual hyperbolic struts 20, as shown in FIG. 6. Each of the male and female members 22, 24 includes a series of concentric rings 34 (e.g., on the upper and lower base plates 16, 18) containing the hyperbolic struts 20. FIG. 6 depicts the footprint of the concentric rings 34 on which the hyperbolic struts 20 are laid. The concentric rings 34 are of increasing diameter from the innermost ring to the outermost ring. The rings 34 are numbered such that the outermost ring is referred to as Ring 1, or R1, and ring numbers increase with decreasing concentric diameters. The ring area is the area contained between two concentric rings 34, as illustrated in FIG. 7. The Ring Area is the area contained between two concentric rings. For example, Area 1,2=Area of Ring 1 (R1)−Area of Ring 2 (R2)

The number of struts is calculated using the following equation:

$$\text{Number of Struts} = \frac{\text{Ring Circumference}}{\text{Strut Diameter}} e^{-0.075(\text{Ring Number})} \sin(24.5°)$$

wherein the K value of −0.075 is the maximum for scaffold response.

The Area of a single strut with a 250 μm diameter is multiplied by the Number of Struts.

The Strut Area/Ring Area (%) is the percentage of area occupied by the struts 20 with respect to their associated ring 34.

Porosity (%) is calculated as 1−Strut Area/Ring Area (%).

The rings 34 can be spaced at any distance apart from one another. In alternate embodiments of the invention, the footprint of scaffold 10 can be of any geometry whilst still utilizing a series of the hyperbolic struts 20. The footprint geometry can be made to resemble that of a vertebral body. The struts 20 can be oriented along any geometrical path, including, but not limited to, a continuous path (e.g., a spiral).

Figure 8:
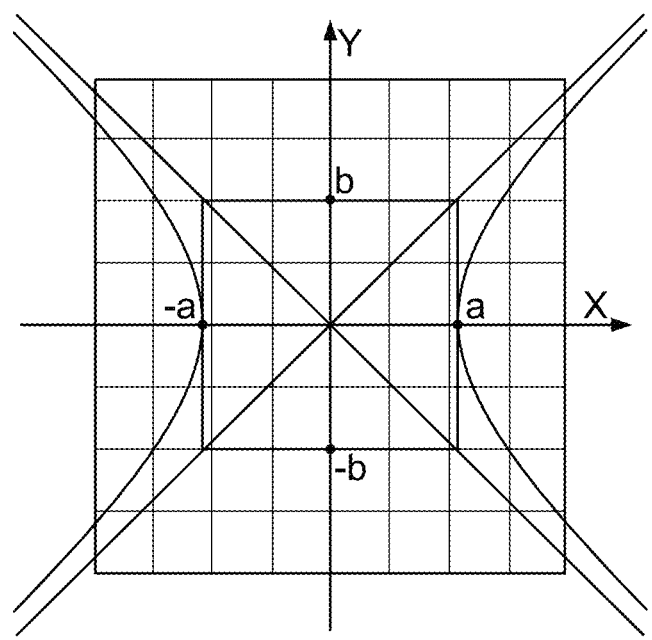
FIG. 8 is a graph showing the parameters to determine the equation of a hyperbolic curved segment in connection the scaffold shown in FIG. 1.

In the preferred embodiment, each individual hyperbolic strut 20 is solid and cylindrical and has a circular cross-sectional area with a constant diameter for the entire length of the strut 20. Each strut 20 follows a hyperbolic equation, as set forth below and illustrated in FIG. 8, which depicts the parameters to determine the equation of the hyperbolic curved segment.

$$(x^2/a^2)-(y^2/b^2)=1$$

Altering the equation can change the arc of the strut 20. In alternate embodiments, the diameter of the strut 20 can be of any desired value. Additionally, the diameter of the strut 20 does not have to remain constant for the entire length of the strut. The struts 20 can also be of any geometry. In the preferred embodiment, the number of struts 20 per ring 34 decreases from the exterior to the interior. The number of struts per ring is calculated using the above equation. In alternate embodiments, any number of struts 20 greater than zero may be used. Additionally, the struts 20 can be made to be solid, hollow, or porous.

In the preferred embodiment, each the struts 20 is angled at ±24.5° in opposite directions at every other ring 34. FIG. 6 depicts the struts 20 oriented at alternating angles of ±24.5 degrees from the base plates 14, 16. An angle of ±24.5° is significant, as this angle is comparable to the fiber angles observed in the annulus fibrosis of the intervertebral disc. In alternate embodiments of the invention, the struts 20 can be oriented at any angle between −180° to +180° in any direction. The hyperbolic shape of the strut 20 in conjunction with the alternating angles allows for one of the struts 20 to cross/engage other surrounding struts 20 at any given location. In alternate embodiments, the struts 20 can engage one another on the same plane or engage on different planes.

Intersecting the struts 20 increases the load carrying capacity of the hyperboloid shell of the scaffold 10. As set out in Example 3 below, this complex interconnection of the struts 20 creates heterogeneous pore sizes measured to be 250-1250 μm, into which pre-donated patient cells (e.g., procured from a biopsy) can be seeded and cultured.

As set out in Example 4 below, the ability of the scaffold 10 to contain pericyte cells was examined and the results showed that cells penetrated throughout the entire scaffold. Cells were not only observed towards the edges but were found at the interior locations of the scaffold as well as at the bottom/inferior surface (see FIGS. 9A, 9B and 9C). The experiment revealed the cytocompatibility of the scaffold 10 and the ability of nutrients to be transferred throughout the scaffold 10 despite its large size.

Alternatively, the scaffold 10 may be used in conjunction with bone graft material (e.g., either autograft bone procured from the patient, or cadaveric allograft bone), or from a synthetic graft material.

In the preferred embodiment, the scaffold 10 has an exponentially increasing porosity from the exterior (40%) to the interior (75%), thereby mimicking the porosity of bone as it transitions from the peripheral rim towards the central regions. Therefore, the preferred embodiment has a translational gradient change in porosity. The increased inner porosity promotes nutrient and media flow to initiate/sustain cell proliferation. The decreased porosity of the exterior regions permits increased strength and a mechanical matrix for cellular containment. In alternate embodiments of the invention, the translational change in porosity can be altered using any formula or regression including, but not limited to, exponential, linear and polynomial.

The method of designing and making the preferred embodiment of the scaffold 10 begins with generating the footprint configuration of the rings 34. A complete hyperbolic strut 20 is then modeled according to the hyperbolic equation disclosed above. The strut 20 is laid at an angle of ±24.5° from the bases of the rings 34. In the preferred embodiment, the strut 20 is then sliced in half and positioned on the outermost ring, R1 (see FIG. 6). In alternate embodiments of the invention, the strut 20 can be sliced along any point of the strut 20 to create a desired height. The struts 20 are then positioned on the following concentric rings 34 at alternating angles of ±24.5°. The desired number of struts 20 per ring 34 is then calculated according to the above equation, and the desired number of struts 20 is revolved around their corresponding rings 34. The struts 20 can be spaced at any distance apart from one another. A circular base plate, with a diameter equal to or greater than the diameter of the outermost ring is then added to the two halves. In alternate embodiments of the invention, the scaffold 10 can be made with or without the base plates 16, 18. The base plates 16, 18 can be on both the top and the bottom (i.e., upper and lower base plates 16, 18, as seen in FIG. 1), the top only or the bottom only. Additionally, each of the base plates 16, 18 can be any shape or thickness and the surfaces of the base plates 16, 18 can be modified to be porous, include spikes, teeth, surface roughness, or other anchoring devices.

Various alternate embodiments of the scaffold 10 of the present invention are disclosed below.

Figure 10:
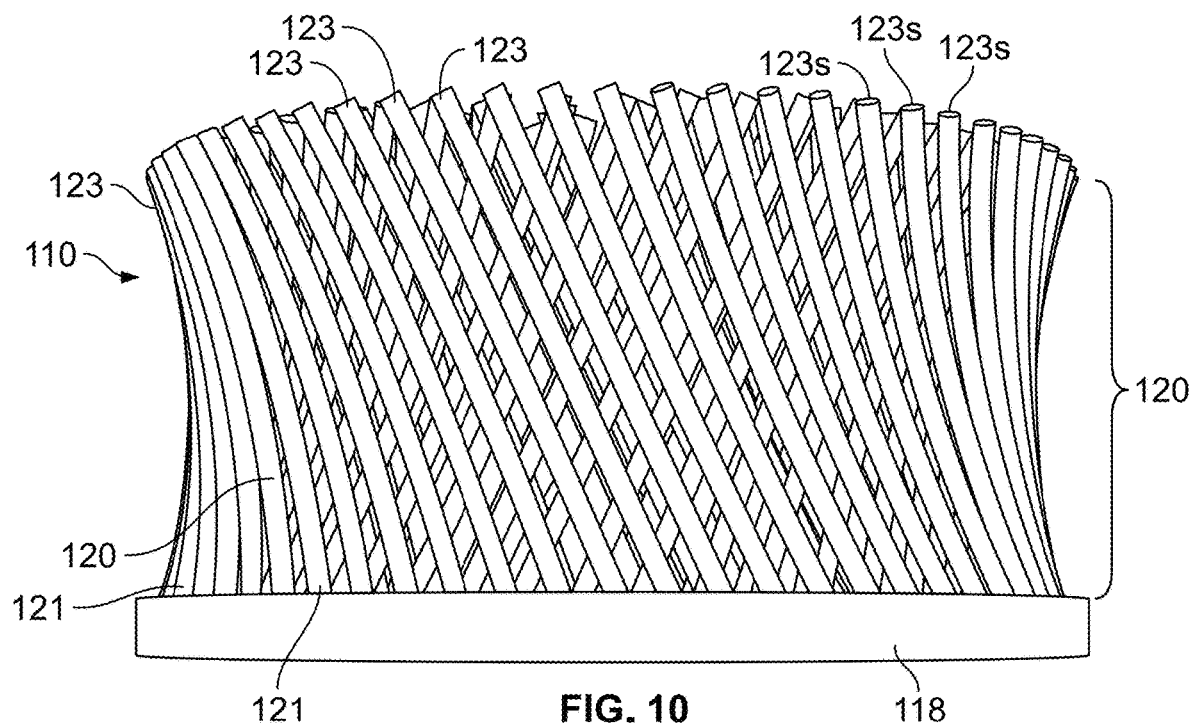
FIG. 10 is a side elevational view of a bone scaffold according to a second embodiment of the present invention.
Figure 11:
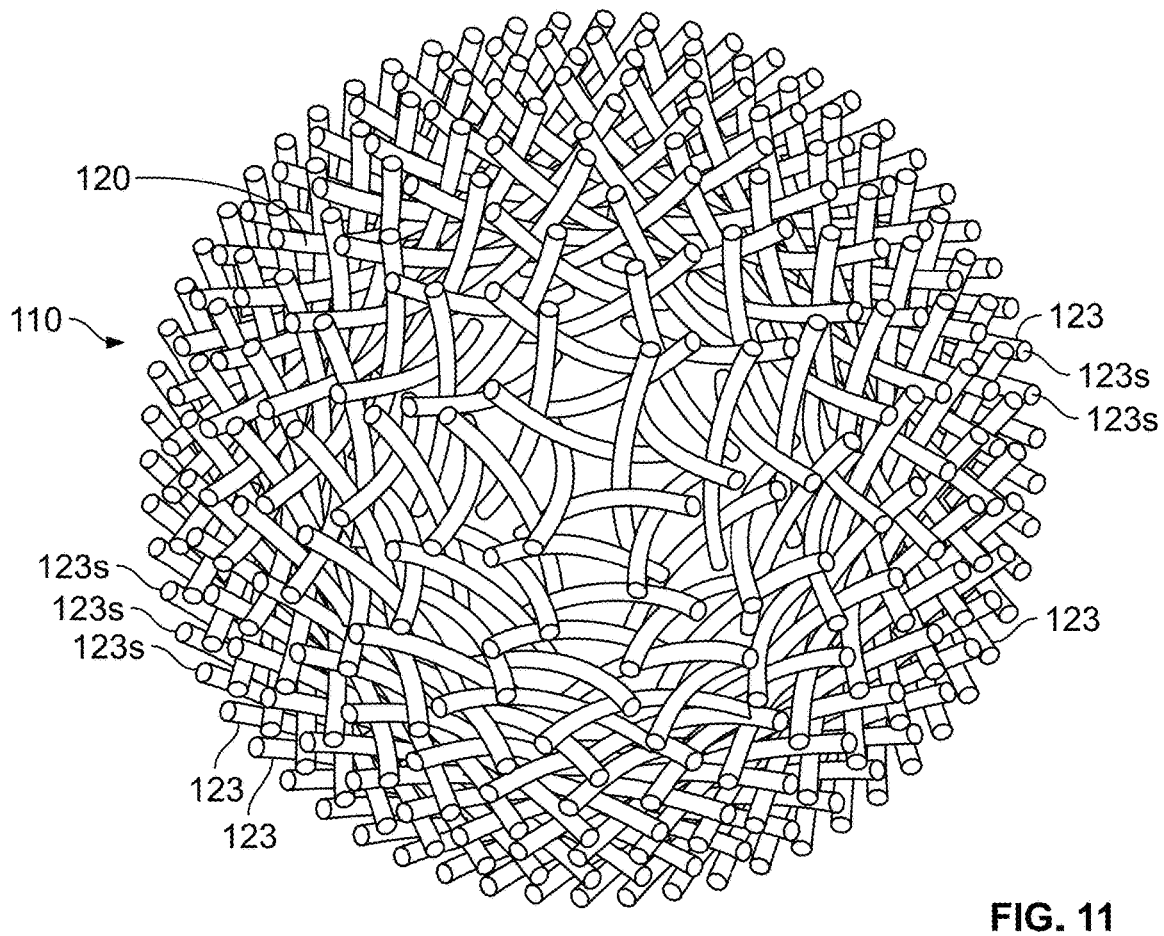
FIG. 11 is a top plan view of the bone scaffold shown in FIG. 10.

FIGS. 10 and 11 depict an alternate embodiment of the invention, wherein the scaffold 110 is generated as one hyperboloid piece. The scaffold 110 includes one (i.e., lower or bottom) base plate 118, and a plurality of uninterrupted hyperbolic struts 120 extending upwardly therefrom and that follow a hyperbolic equation. The hyperbolic struts 120 each have a first end 121 secured to the base plate 118 and a second end 123 that is opposite the first end 121. Unlike the first ends 121, the second ends 123 are free ends, each having an exposed end surface 123s. The scaffold 110 has no upper base plate, whereby the exposed end surfaces 123s remain exposed. This open faced exposure can aid in osteointegration, cell seeding, and bone graft incorporation.

The spatial configuration of struts 120 can be observed in FIG. 11. The struts 120 are more tightly oriented at the periphery of the scaffold 110 than they are proximate its center, revealing the translational porosity gradient of the scaffold 110.

Figure 12:
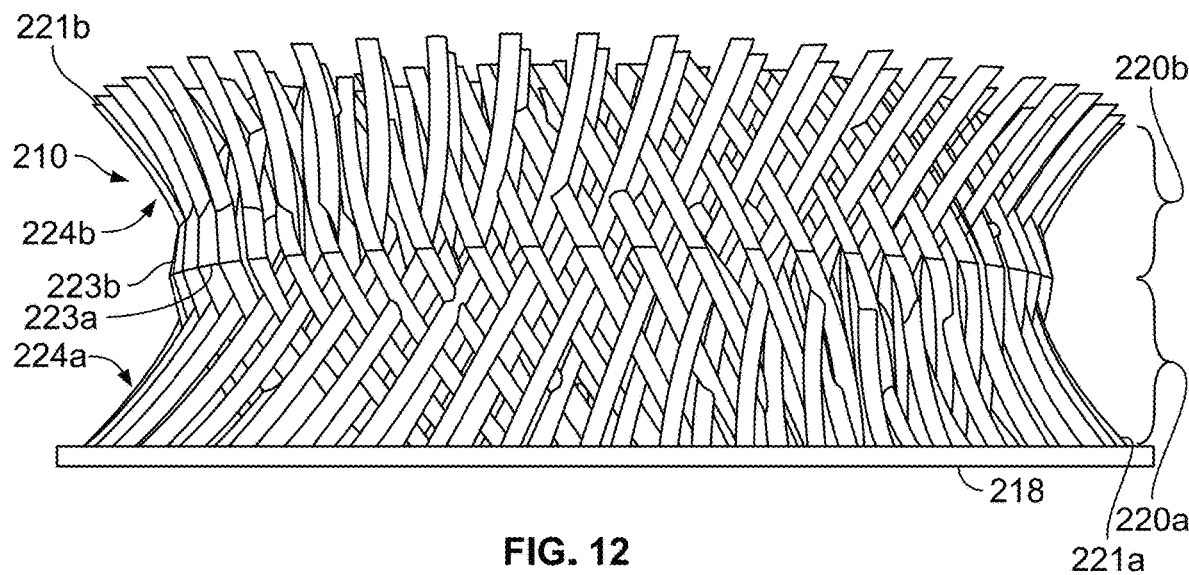
FIG. 12 is a side elevational view of a fully assembled bone scaffold according to a third embodiment of the present invention.
Figure 13:
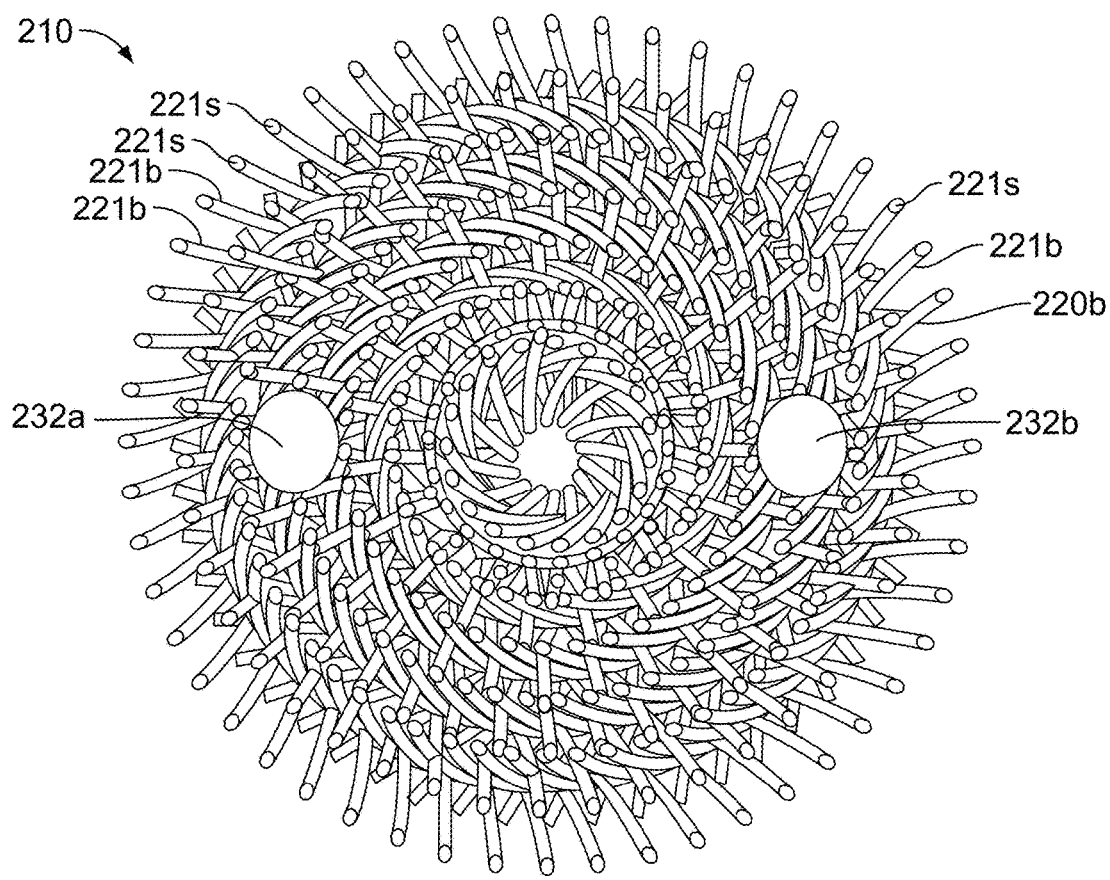
FIG. 13 is a top plan view of the bone scaffold shown in FIG. 12.

FIGS. 12 and 13 depict another alternate embodiment of the scaffold 210. While the scaffold 210 is one hyperboloid piece, its assembly is similar to the scaffold 10 having male and female members or halves. The scaffold 210 includes a first female member 224a that is similar to the female member 24 shown in FIGS. 4 and 5. The first female member 224a has a plurality of struts 220a that are cut to achieve a desired reduced (e.g., half or partial) height. The struts 220a each have a first end 221a secured to a first base plate 218 and a second end 223a that is opposite the first end 221a. Unlike the first ends 221a, the second ends 223a are free ends, each having an exposed end surface (not shown).

The scaffold 210 further includes a second female member 224b that is formed to be substantially identical to the first female member 224a. The second female member 224b has a plurality of struts 220b that are cut to achieve a desired reduced (e.g., half or partial) height. Each of the struts 220b has a first end 221b that is initially secured to a second base plate (not shown) and a second end 223b that is opposite the first end 221b. The second ends 223b are free ends, each having an exposed end surface (not shown).

The second female member 224b is superimposed onto the first female member 224a such that the struts 220a, 220b mate and align along their respective exposed end surfaces (see FIG. 12), similar to the configuration described above in connection with the scaffold 10. In alternate embodiments, the struts 220a, 220b can be sliced along any point of the strut curve to generate a desired height or geometry. The struts 220a, 220b can be sliced and mated along any point along the length thereof.

The first and second female members 224a, 224b can be mated in the CAD model itself or through other means during fabrication to generate one hyperboloid part. Once the second female member 224b is superimposed on the first female member 224a, the base plate of the second female member 224b is removed (i.e., cut off), whereby the surfaces 221s of the first ends 221b are also exposed. The scaffold 210 has one (i.e., lower or bottom) base plate 218.

With reference to FIG. 13, each of the female members 224a, 224b includes two cylindrical bores, or holes, 232a, 232b that extend upwardly from the base plate 218, and are formed and surrounded by the struts 220. In this embodiment, the bores 232a, 232b provide a means for vascularization and nutrient transfer.

The scaffold 210 was tested in static compression for its mechanical integrity (see Example 5 below). The average yield load was calculated to be 4900±51 N at an average yield deformation of 1.15±0.38 mm. The scaffold yield strain was calculated to be 12±3.5%. The energy dissipation or area under the curve was 1.72±0.18 J. Scaffold stiffness was calculated to be 8600±580 N/mm. The results indicate that alternate embodiments of the invention can withstand over four times body weight.

Additional alternate embodiments of the scaffolds 10, 110, 210 are included within the scope of the claimed invention. Outermost layers of the scaffolds 10, 110, 210 can be made non-porous, so as to act as a shell for containment. The overall hyperboloid shape of the scaffolds 10, 110, 210 can also be made through the use of straight struts laid at an angle. With respect to the struts, achievement of an overall hyperbolic type strut can potentially be made through a series of shorter connected linear segments. Additionally, the strut geometry, dimensions, and equation do not have to remain uniform within the same embodiment. Overall modifications can be made after the struts have been oriented. Vasculature can be added to increase nutrient flow. Stabilizing/strengthening features may also be included. In alternate embodiments, the surface of the struts (or surfaces of the scaffolds 10, 110, 210, respectively, as a whole) can be sliced at patient specific angles to match the angle of lordosis or kyphosis per patient. The scaffolds 10, 110, 210 may be stackable. Stacking may be done in the spinal column if the patient needs successive vertebrectomies. Any number of posts or alignment configurations may be used. In alternate embodiments, alignment can also be achieved by altering the overall surface geometry or height of each member (via altering the heights of individual struts). The posts can be solid, hollow, or porous. Additionally, the posts and/or struts can be laid on top of the base plate or embedded within it. Further, the bores/holes can be of any desired height.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, temperature is in degrees centigrade, force is measured in Newtons (N), and energy is measured in Joules (J).

Figure 14B:
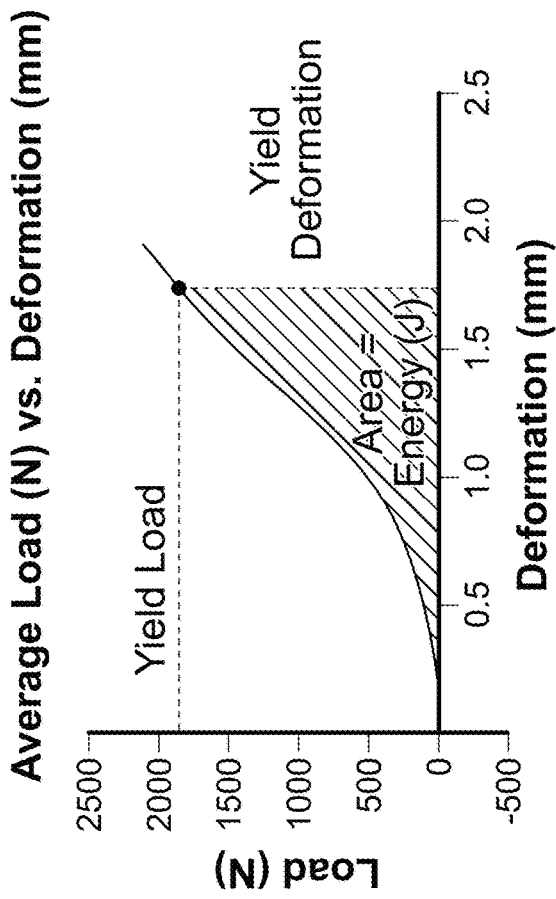
FIG. 14B is a graph showing load versus displacement response displaying yield load, yield deformation and energy as the area under the curve, as discussed in Example 1.
Figure 14A:
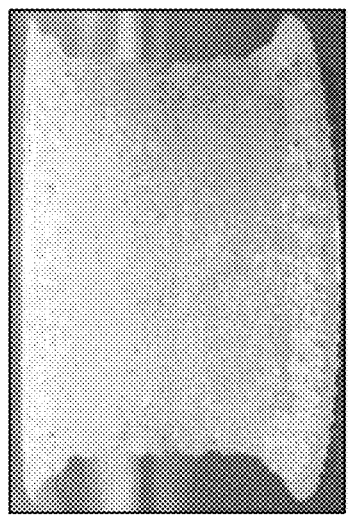
FIG. 14A is a photograph of a scaffold according to an embodiment of the present invention that has been 3D printed from PLA, as discussed in Example 1 herein.
Figure 14C:
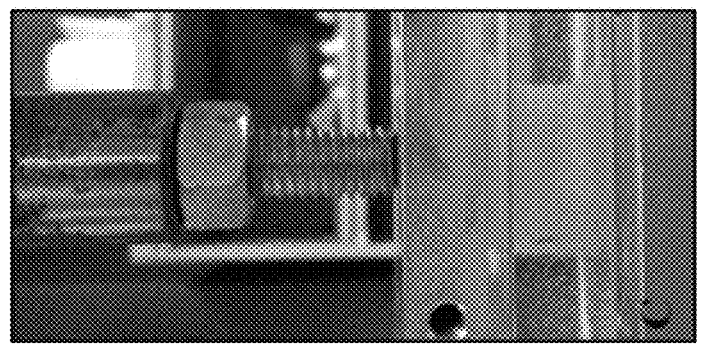
FIG. 14C is a photograph of an experimental set-up of the scaffold shown in FIG. 14A in media, aligned with a loading axis of a materials testing machine, as discussed in Example 1.

Example 1—Static Mechanical Properties of 3D Printed Trans-Modular PLA Scaffold for Bone Grafting Applications Methods Scaffolds were 3D printed using a Makerbot Replicator (Makerbot Industries, LLC, Brooklyn, N.Y.) from PLA filament at a layer thickness of 0.08 mm. Scaffolds were designed and printed in two sections to create a hyperboloid shape (see FIG. 14A). The design is composed of a series of concentric rings containing hyperbolic struts of decreasing number from the exterior to the interior of the scaffold. The porosity of the scaffold increases exponentially from the exterior (40%) towards the interior (75%), thereby mimicking the porosity of the vertebra as one transitions from the peripheral rim toward the central regions. To determine the static mechanical properties, seven scaffolds were immersed in media (hMSC High Performance Media Kit, RoosterBio Inc, Frederick, Md.) and placed between two plates on the load cell of a materials testing machine (Bose ELF 3300, Minnetonka, Minn.) in alignment with the loading axis (see FIG. 14C). Scaffolds were statically loaded in displacement control at a rate of 1 mm/s with load versus displacement data continuously acquired. Load versus displacement curves were plotted and analyzed for each scaffold to determine the yield load, yield displacement, yield strain, stiffness and energy dissipation, calculated as the area under the curve (see FIG. 14B).

Results

Table 1 lists the yield load, yield displacement, % strain, energy, and stiffness of the scaffold under static loading (N=7).

TABLE 1

Results of static test on scaffold showing yield load, yield deformation, yield strain, energy, and stiffness.

| | Scaffold Means (N = 7) |
|---|---|
| Yield Load (N) | 1691 +/− 93 |
| Yield Deformation (mm) | 1.91 +/− 0.2 |
| Yield Strain (%) | 11 +/− 1 |
| Energy (J) | 0.87 +/− 0.09 |
| Stiffness (N/mm) | 1959 +/− 267 |

Figure 15:
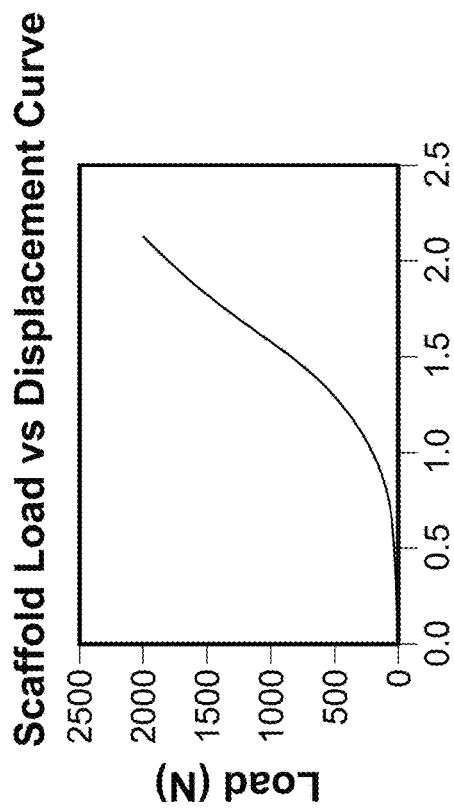
FIG. 15 is a graph showing load versus displacement response of a scaffold in static loading, as discussed in Example 1.

A typical loading response is shown in FIG. 15 and depicts load versus deformation curve. The average yield load was calculated to be 1691+/−93 N at an average yield displacement of 1.91+/−0.2 mm. The scaffold yield strain was calculated to be 11+/−1%. The energy dissipation or area under the curve was 0.87+/−0.09 J. Scaffold stiffness was calculated to be 1959+/−267 N/mm.

Discussion

The mechanical properties of 3D printed PLA scaffolds were examined under static loading. A scaffold yield load of 1691 N is acceptable, as bone grafts in the spine should be able to withstand loads of daily activity. Axial loads in the lumbar spine have been reported to be 200 N in the relaxed supine position and up to 1000 N in the upright position (see Wilke, H., J., Neef, P., Caimi, M., Hoogland, T., Claes, L., 1999, "New intradiscal pressure measurements in vivo during daily activities", Spine, 24(8):755-762). A study on static compressive testing of PEEK interbody devices yield loads in the range of 2500-3000 N which compares favorably to these results. Additionally, the scaffold stiffness of 1959+/−267 N/mm was within a comparable range to the 2500 N/mm stiffness reported for the PEEK interbody device of comparable overall geometry (see Valdevit, A., Dawoud, M., 2015, "Intervertebral implant performance based on dynamic stiffness response", Am. J. Biomed. Eng, 5(3):79-85). With respect to energy, the scaffold energy dissipation of 0.87 J also compares favorably with the values reported for bovine femur energy dissipation 0.5+/−0.1 J when loaded to fracture. Scaffold strain of 11+/−1% also compared favorably to strain values reported for bone (see Yan, J., Mecholsky Jr., J., J., Clifton, K., B., 2007, "How tough is bone? Application of elastic-plastic fracture mechanisms to bone", Bone, 40: 479-484). A study analyzing the failure behavior of cortical versus trabecular bone found strains of 22.9+/−7.4% and 36.6+/−14% for cortical and trabecular bone, respectively (see Szabo, M E., Zekonyte, J., Katsamenis OL., Taylor, M., 2011, "Similar damage initiation but different failure behavior in trabecular and cortical bone tissue", J Mech Behav Biomed Mater, 4(8):1987-96).

Significance

These surgically sized and mechanically functional 3D printed scaffolds may alleviate the morbidity associated with graft harvesting and the limited supply of cadaveric grafting. Further, as the scaffold is comprised of a strut construct, reduction of stress shielding via energy dissipation and fluid transfer through the scaffold may increase rate of incorporation.

Figure 16C:
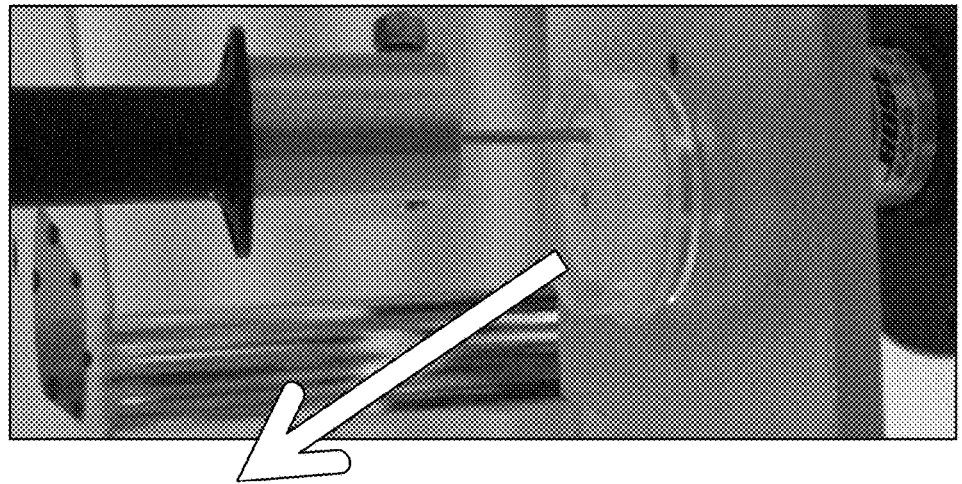
FIG. 16C is a photograph of an indentation test experimental set-up on a materials testing machine, as discussed in Example 2.
Figure 16B:
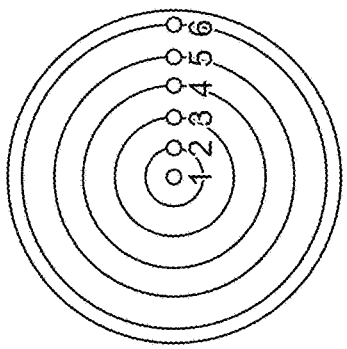
FIG. 16B is a schematic showing indentation test locations at Sites 1-6 the scaffolds, as discussed in Example 2.
Figure 16A:
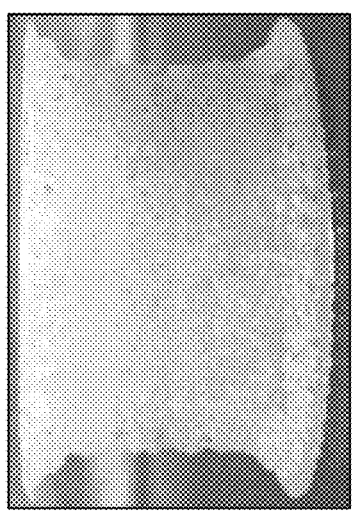
FIG. 16A is a photograph of a scaffold according to an embodiment of the present invention that has been 3D printed from PLA, as discussed in Example 2 herein.
Figure 16D:
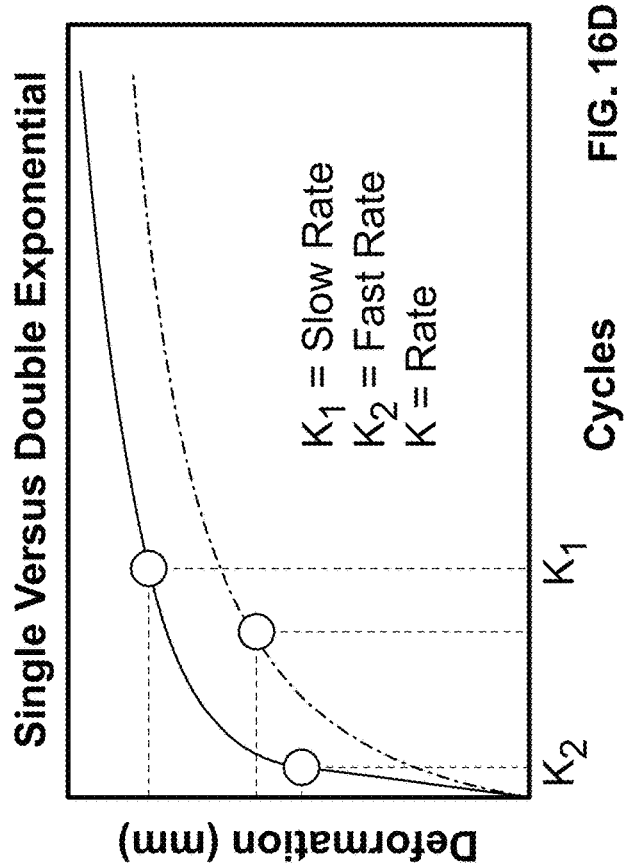
FIG. 16D is a graph showing single versus double exponential of rate of deformation (K), wherein double exponential denotes a two-phased response, as discussed in Example 2.

Example 2—Dynamic Analysis of 3D Printed Trans-Modular PLA Scaffolds for Bone Tissue Engineering Applications in the Spine Methods Scaffolds were fabricated from PLA filament using a Makerbot Replicator 3D printer (Makerbot Industries, LLC, Brooklyn, N.Y.) at a layer thickness of 0.08 mm. Scaffolds have hyperboloid geometry (see FIG. 16A) and have exponentially increasing porosity from the exterior (40%) towards the interior (75%), replicating the strength changes of the vertebral endplate. Mechanical properties of the bulk scaffold assembly, as well as regional mechanical variations within the scaffold geometry were elucidated via dynamic compressive, sinusoidal loading tests. Six scaffolds were immersed in media (hMSC High Performance Media Kit, RoosterBio Inc, Frederick, Md.) and subjected to cyclic compressive loading from −10N to −100N (0.2 MPa) for 555 cycles at 1 Hz using a 31 mm diameter indentor fixed to a materials testing machine (Bose ELF 3300, Minnetonka, Minn.). Load versus deformation data was recorded at cycle 5 and at 25 cycle intervals thereafter. Deformation changes over the applied loading cycles were calculated for each scaffold. To elucidate regional mechanical variations, 6 additional scaffolds were fabricated. For each scaffold, 6 indentation sites, identified as locations 1-6 (see FIG. 16B), were subjected to 530 cycles of cyclic compressive loading from −1 to −10N (0.8 MPa) at 1 Hz using a 2 mm indentor fixed to the actuator of a materials testing machine (Bose ELF 3200, Minnetonka, Minn.) (see FIG. 16C). Load versus deformation data was recorded at cycle 10 and at 20 cycle intervals thereafter. Deformation changes over the applied loading cycles were averaged for Sites 1-2, Sites 3-4 and Sites 5-6. The bulk and regional deformation data was subjected to non-linear exponential regression employing a single or dual exponential decay function. Selection of the appropriate model was based upon the F-test ($P<0.05$) for the comparison of the fitted data. The resulting exponential parameters were identified as K Fast and K Slow (see FIG. 16D) (for dual exponential functions), K (for single exponential functions, $Y_0$ (initial deformation), and Plateau (asymptotic deformation limit). All exponential parameters were analyzed using a one-way ANOVA with a Tukey post hoc test to compare sites.

Results

Figure 17B:
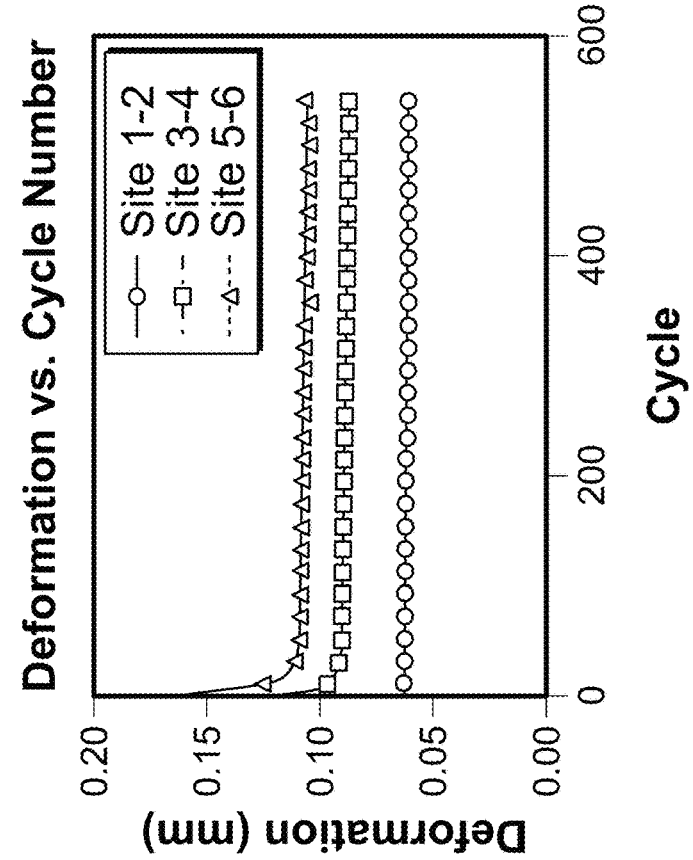
FIG. 17B is a graph showing deformations versus cycle number at test location Sites 1-6, as discussed in Example 2.
Figure 17A:
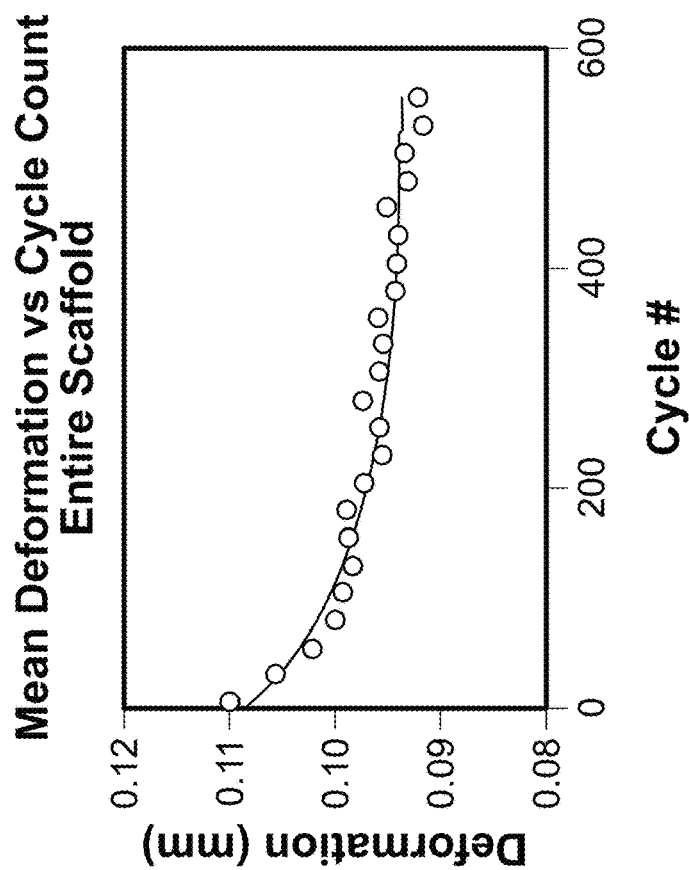
FIG. 17A is a graph showing mean deformation versus cycle number for the whole scaffold shown in FIG. 16A, as discussed in Example 2.
Figure 17E:
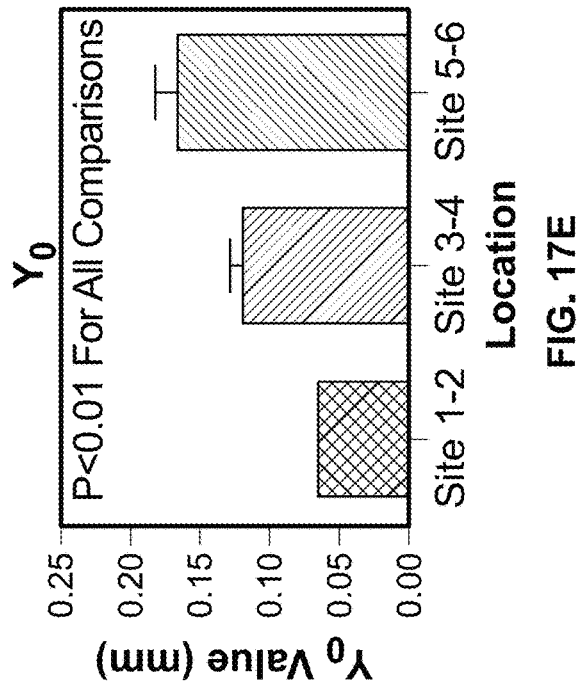
FIG. 17E is a graph showing initial deformation $Y_0$ at test location Sites 1-6, as discussed in Example 2.
Figure 17F:
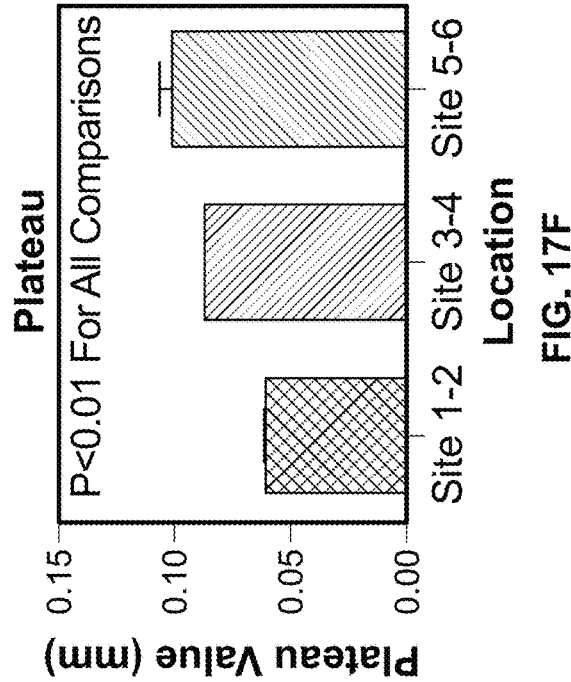
FIG. 17F is a graph showing the plateau value for test location Sites 1-6 having significant differences ($P<0.01$), as discussed in Example 2.
Figure 17C:
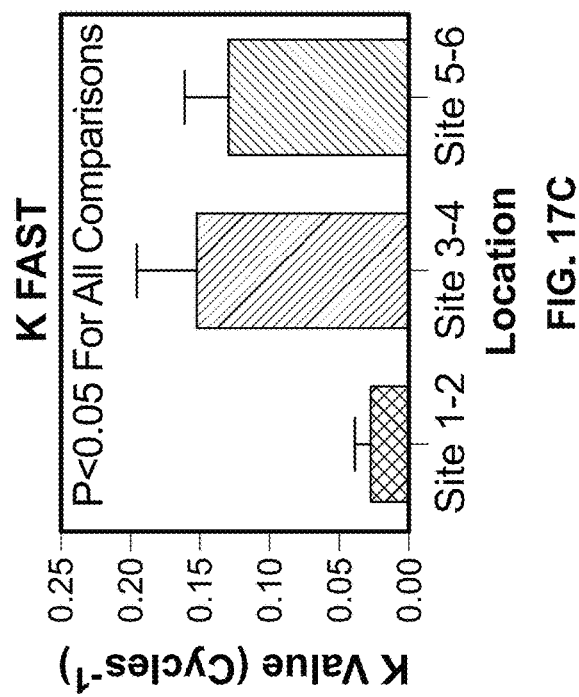
FIG. 17C is a graph showing the test location Sites 1-6 being statistically different for K Fast ($P<0.05$), as discussed in Example 2.
Figure 17D:
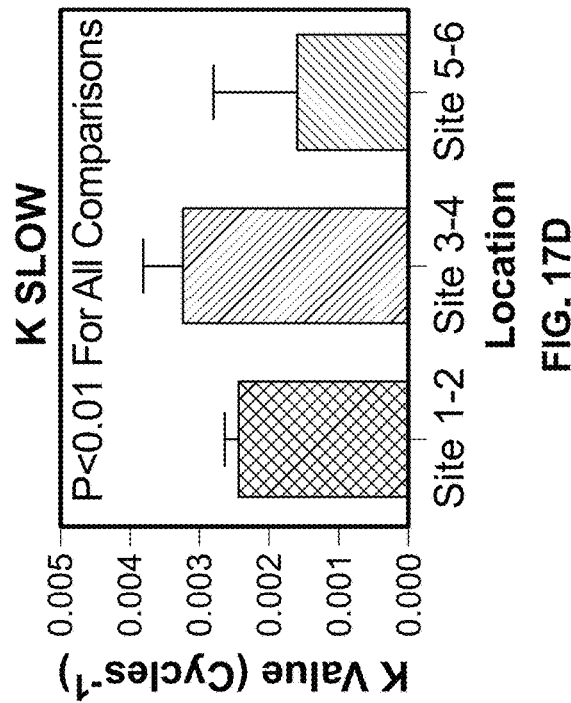
FIG. 17D is a graph showing the test location Sites 1-6 having significant differences for K Slow ($P<0.01$), as discussed in Example 2.

With respect to the bulk fatigue test, the mean deformation versus cycle number is shown in FIG. 17A and depicts a single exponentially decreasing deformation over the applied loading cycles. The parametric assessment of the non-linear regression revealed an initial deformation, $Y_0$, of 0.11 mm. The scaffold deformed at a rate (K value) of 0.008 mm/-cycle until the deformation plateaued at 0.09 mm, hence deforming a total span of 0.02 mm throughout the course of the experiment. The results of the regional indentation fatigue tests depict a trend of exponentially decreasing deformation with cycle number for all test sites (see FIG. 17B). A two-phased rate of deformation was preferred, and resulted in rates called K Fast and K Slow. The center sites 1-2 have a significantly decreased K Fast compared to the other test sites ($P<0.05$ for all comparisons) (see FIG. 17C). For K Slow, sites 5-6 show a decreased rate of deformation compared to other test sites ($P<0.01$ for all comparisons) (see FIG. 17D). Statistically significant differences between all loading sites were observed for both the $Y_0$, initial deformation, ($P<0.01$) (see FIG. 17E) and Plateau ($P<0.01$) (see FIG. 17F).

Discussion

The results of the bulk scaffold fatigue test displayed a single exponential decay of decreasing deformation versus cycle number, indicating an increase in stiffness (or strain hardening) with cycle number. A similar trend of increasing stiffness over cycle number was observed in PEEK and titanium intervertebral devices when loaded in fatigue (see Valdevit, A., Dawoud, M., 2015, "Intervertebral implant performance based on dynamic stiffness response", Am. J. Biomed. Eng, 5(3):79-85). With respect to the indentation fatigue test, the two-phased rate of deformation is of interest. Bone is composed of two phases which affect its mechanical properties; the solid phase and the fluid phase, which are represented in this study by K Fast and K Slow, respectively. An increased K value, or rate of deformation, indicates a reduced amount of cycles required for the scaffold to stiffen and settle. The decreased K Fast value at sites 1-2 compared to the outer sites 3-4 and 5-6 demonstrates a slow initial settling which is expected as the increased amount of fluid at this site will take longer to dissipate outwards, causing a longer amount time to stiffen and settle. The increased K Fast value at sites 3-4 and 5-6 indicate faster initial stiffening. As K Slow represents the fluid phase, the reduced K Slow value at outer sites 5-6 is expected as the outer locations have reduced fluid and will stiffen faster, initially. It has been well documented that regional structural properties of the endplate are such that the posterior is stronger than the anterior, and the periphery is stronger than the center. However, when the endplate is removed thus exposing the underlying trabecular bone, the regional structural properties change. In lumbar vertebral bodies, it has been reported that a greater decrease in failure load posteriorly and stiffness laterally is observed when the endplate is removed (see Oxland, T R., Grant, J P., Divorak, M F., Fisher, C G., 2003, "Effects of endplate removal of the structural properties of the lower lumbar vertebral bodies", Spine, 28(8): 771-777). The same trend is observed if one considers the internal loading sites of the scaffolds as the deformation increases from the center sites 1-2 to the middle sites 3-4 and outer sites 5-6. It is surmised that the reduced amount of fluid present in the condensed stiffer bone of the vertebral periphery allows for stiffening to occur more rapidly. As these scaffolds were tested in media, the same can be said that as is more fluid within the center (higher porosity) than at the periphery.

Significance

Scaffolds mechanically comparable to bone may reduce stress shielding and improve natural energy and fluid transfer through grafts in spinal fusion.

Example 3—Pore Size Verification

Three scaffolds were microscopically examined using a Nikon SMZ 1500 under 2× magnification. Pore diameters and areas were measured and averaged at each of the scaffold center and edge locations, as well as the cross section. Pore sizes were also measured on another scaffold under 10× magnification. The measured pore diameters and areas are provided in Table 2. The scaffold has heterogeneous pore sizes, between about 250-1250 µm, which allow for cell attachment as well as nutrient flow throughout the entirety of the scaffold. The minimum pore size required to regenerate mineralized bone is 100 µm. Pore sizes between 300-500 µm have been shown to be optimal for hMSC attachment. Larger pore sizes, around 1000 µm will provide vascularization and are beneficial for nutrient transfer throughout the scaffold. Additionally, the porous surface improves osteointegration between the implant and surrounding natural bone, increasing the mechanical stability of the implant/bone interface.

TABLE 2

Pore diameter and pore area measurements

|  | Pore Diameter (µm) | Pore Area (µm$^2$) |
|---|---|---|
| 2X |  |  |
| Center | 1014.6 ± 305.7 (N = 16) | 1,046,439 ± 592,805 (N = 14) |
| Edge | 1138.0 ± 254.6 (N = 16) | 1,907,701 ± 1,302,769 (N = 14) |
| Cross section | 408.94 ± 70.63 (N = 8) |  |
| 10X |  |  |
| Center | 291.9 ± 16.57 (N = 7) |  |
| Edge | 336.2 ± 27.99 (N = 3) |  |
| Average Center | 794.6 ± 423.6 (N = 23) |  |
| Average Edge | 1011 ± 380 (N = 19) |  |

Example 4—Cellular Retainment Verification

Figure 9A:
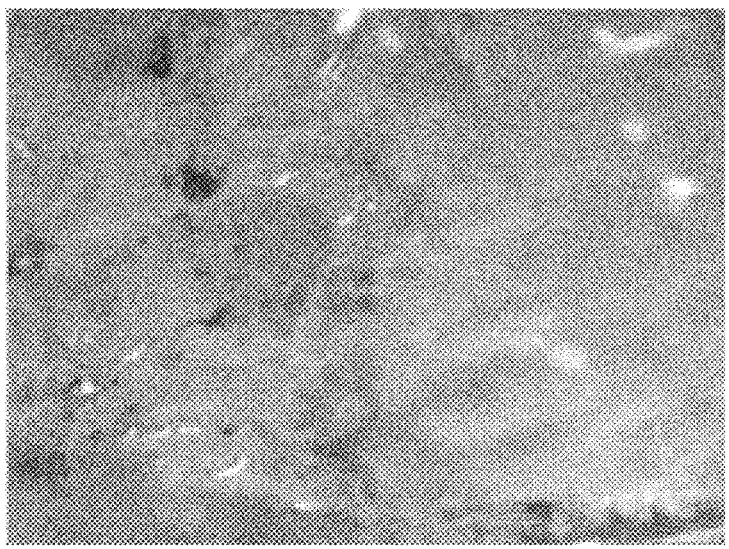
FIG. 9A is a photomicrograph showing a cross-sectional image of a scaffold according to an embodiment of the present invention, as penetrated by pericyte cells and stained with methylene blue, and observed under 4× magnification.
Figure 9B:
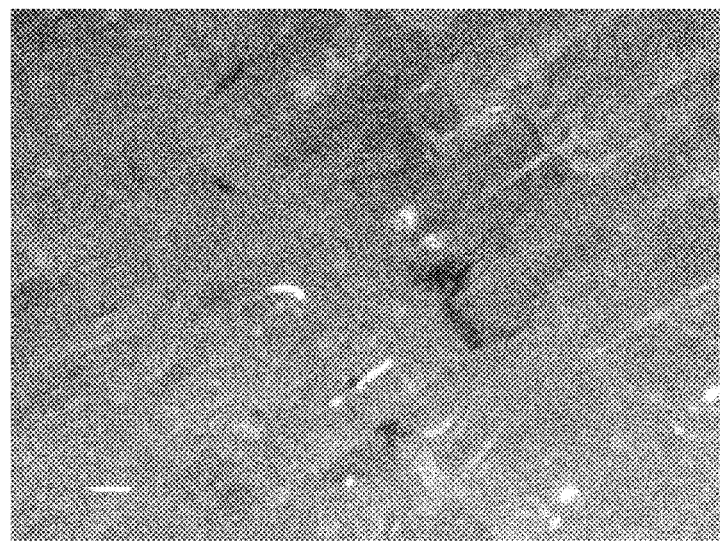
FIG. 9B is a photomicrograph showing an image of the inferior surface of a scaffold according to an embodiment of the present invention, as penetrated by pericyte cells and stained with methylene blue, and observed under 4× magnification.
Figure 9C:
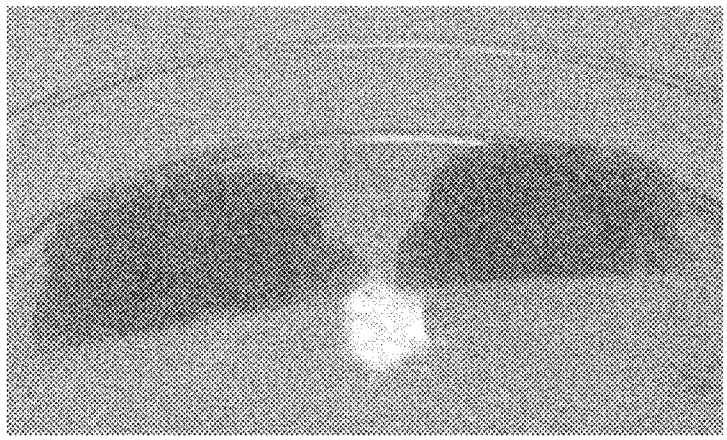
FIG. 9C is a photograph showing a cross-sectional image of a scaffold according to an embodiment of the present invention, as penetrated by pericyte cells and stained with methylene blue.

The scaffold was placed in a 60 mm diameter well plate by 10 mm tall, and sterilized in 70% isopropyl alcohol for 24 hours. It was then washed three times with DMEM with 10% fetal bovine serum and 1% stryptomyocin. Human placental pericytes (Promo Cell) were used in this experiment. Human placental perictytes were cultured in T75 flask using perictye growth medium with added supplement, and 1% stryptomycin and penicillin until 80% confluency in a humidified incubator buffered with 5% CO2. The pericytes were detached using Detach Kit according to manufacturer's instructions. Cells were seeded onto the scaffold at a concentration of 8×10$^5$ cells/mL. A total of 5 mL was added to the scaffold. The seeded scaffold was let to sit for 2 hours before being placed in another 60 mm dish on a 16 rpm rotary bioreactor (Synthecon Inc., Houston, Tex.). The 60 mm dish containing the seeded scaffold was placed in the bioreactor at a slight angle to allow for increased media flow throughout the entire system, and cultured for a total of 7 days in an incubator at 37° C. and 5% CO2. The media was changed on days 3 and 5. No bacteria or cells were found in the dish, indicating good cell attachment. The cells were fixed using 4% paraformaldehyde on day 7 and stained with methylene blue for a half hour. The scaffold was washed with PBS until no more dye could be removed. The scaffold was sliced in half and imaged using a Nikon SMZ 1500 under 4× magnification. Cells were observed to have penetrated throughout the scaffold. Cells were not only observed towards the edges but were found at the interior locations of the scaffold as well as at the bottom/inferior surface (FIGS. 9A, 9B and 9C). The experiment revealed the cytocompatibility of the scaffold and the ability of nutrients to be transferred throughout the scaffold despite the large size.

Example 5-3D Printed Polymeric Bone Scaffolds Withstand Physiological Loads in the Spine Under Static Loading Materials and Methods Scaffolds were 3D printed using a Makerbot Replicator (Makerbot Industries, LLC, Brooklyn, N.Y.) from PLA filament. Scaffolds were designed and printed in two sections to create a hyperboloid shape. To determine the static mechanical properties, five scaffolds underwent a static compression test in accordance with ASTM Standard F2077 for Intervertebral Body Fusion Devices (see ASTM Standard F2077, 2014, "Intervertebral Body Fusion Devices", ASTM International, West Conshohocken, Pa., 2014, DOI: 10.1520/F2077-14, www.astm.org). Scaffolds were placed between two metal plates on the load cell of a materials testing machine (MTS 858 Mini Bionix, Eden Prairie, Minn.) in alignment with the loading axis. Scaffolds were statically loaded in displacement control at a rate of 25 mm/min with load versus displacement data acquired at a 40 Hz sampling rate. Load versus displacement curves were plotted and analyzed for each scaffold to determine the yield load, yield displacement, yield strain, stiffness and energy dissipation, calculated as the area under the curve.

Results and Discussion

Table 3 lists the yield load, yield displacement, % strain, energy, and stiffness of the scaffold under static loading (N=5). The average yield load was calculated to be 4900±51 N at an average yield deformation of 1.15±0.38 mm. The scaffold yield strain was calculated to be 12±3.5%. The energy dissipation or area under the curve was 1.72±0.18 J. Scaffold stiffness was calculated to be 8600±580 N/mm. The mechanical properties of 3D printed PLA scaffolds were examined under static loading. A scaffold yield load of 4900 N is approximately 2.5 times the failure load reported with the vertebral endplate (see Kwon, A J. J Neurosurg Spine, 2016; 29:1-7). Axial loads in the lumbar spine can range between 800 N standing upright to upwards of 3000 N during active lifting (see Arjmand, N. Clin Biomech (Bristol, Avon), 2012; 27:537-544). With respect to energy, the scaffold energy dissipation of 1.72±0.18 J compares favorably with the values reported for human lumbar vertebrae energy dissipation 1.73±1.13 J when loaded to failure (see Wegrzyn, J. J Bone Miner Res, 2011; 26(4):739-46). Scaffold strain of 12±3.5% also compared favorably to strain values reported for bone. A study analyzing the failure behavior of cortical versus trabecular bone found strains of 22.9±7.4% and 36.6±14% for cortical and trabecular bone, respectively (see Szabo, M E. J Mech Behav Biomed Mater, 2011; 4(8):1987-96).

TABLE 3

Results of the static loading test averaged across five scaffolds, calculated from load versus deformation data collected in the experiment.

|  | Scaffold Means (N = 5) |
| --- | --- |
| Yield Load (N) | 4900 +/− 51 |
| Yield Deformation (mm) | 1.15 +/− 0.38 |
| Yield Strain (%) | 12 +/− 3.5 |
| Energy (J) | 1.72 +/− 0.18 |
| Stiffness (N/mm) | 8600 +/− 580 |

Yield load 4900±51 N, yield displacement 1.15±0.38 mm, yield strain 12±3.5%, energy 1.72±0.18 J, and stiffness 8600±580 N/mm values are shown.

CONCLUSIONS

These surgically sized and mechanically functional 3D printed scaffolds may alleviate the morbidity associated with graft harvesting and the limited supply of cadaveric grafting. Scaffolds mechanically comparable to vertebral bone may reduce stress shielding and improve natural energy transfer through grafts in spinal fusion. Future work involves verification of biological efficacy for fusion and mechanical evaluation during accelerated degradation studies.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It will be understood that the embodiments described herein are merely exemplary and that a person skilled in the art may make many variations and modifications without departing from the spirit and scope of the invention. All such variations and modifications are intended to be included within the scope of the invention and the appended claims.

We claim:

1. A spinal fusion bone scaffold, comprising:
a first member including a first base plate and a first plurality of struts, each of said first plurality of struts having a first end engaging said first base plate, and a second end opposite said first end, each of said second ends of said first plurality of struts being a free end having a first exposed end surface, and each of said first plurality of struts being configured to form at least part of a hyperbolic curve such that said bone scaffold includes an overall optimized hyperboloid shape having an outer diameter and an inner waist diameter; and
a second member including a second plurality of struts, each of said second plurality of struts having a first end and a second end opposite said first end of each of said second plurality of struts, each of said second plurality of struts being configured to form at least part of the hyperbolic curve, and connecting means for connecting said second member to said first member, wherein each of said second ends of said second plurality of struts is a free end having a second exposed end surface, and wherein said second exposed end surfaces are aligned and in contact with said first exposed end surfaces of said first plurality of struts of said first member, so as to complete the hyperbolic curve while generating an overall hyperboloid geometry of said bone scaffold.

2. The spinal fusion bone scaffold of claim 1, wherein said second member includes a second base plate, said second base plate engaging said first ends of said second plurality of struts.

3. The spinal fusion bone scaffold of claim 2, wherein said connecting means includes at least one alignment post extending from said first base plate of said first member, and at least one cylindrical bore extending from said second base plate, said at least one cylindrical bore being dimensioned to receive insertably said least one alignment post, whereby said first member and said second member are aligned with one another and secured together.

4. The spinal fusion bone scaffold of claim 1, further comprising an exterior, an interior, and a translational gradient change in porosity, said porosity exponentially increasing from said exterior to said interior, whereby said translational gradient change is configured to mimic a porosity pattern of bone as it transitions from a peripheral rim towards central regions of the bone.

5. The spinal fusion bone scaffold of claim 1, wherein said scaffold is fabricated from poly-lactic acid (PLA).

6. The spinal fusion bone scaffold of claim 5, wherein said scaffold is fabricated via 3D printing.

7. The spinal fusion bone scaffold of claim 1, wherein said scaffold is fabricated from a biocompatible material selected from the group consisting of metals, ceramics, polymers and combinations thereof.

8. A spinal fusion bone scaffold, comprising a first member including a first base plate and a first plurality of struts, each of said first plurality of struts having a first end engaging said first base plate, and a second end opposite said first end, each of said first plurality of struts being configured to form at least part of a hyperbolic curve such that said bone scaffold includes an overall optimized hyperboloid shape having an outer diameter and an inner waist diameter, and wherein said first ends of said first plurality of struts engage said first base plate at alternating angles of ±24.5 degrees.

9. The spinal fusion bone scaffold of claim 8, further comprising an exterior, an interior, and a translational gradient change in porosity, said porosity exponentially increasing from said exterior to said interior, whereby said translational gradient change is configured to mimic a porosity pattern of bone as it transitions from a peripheral rim towards central regions of the bone.

10. The spinal fusion bone scaffold of claim 8, wherein said scaffold is fabricated from poly-lactic acid (PLA).

11. The spinal fusion bone scaffold of claim 10, wherein said scaffold is fabricated via 3D printing.

12. The spinal fusion bone scaffold of claim 8, wherein said scaffold is fabricated from a biocompatible material selected from the group consisting of metals, ceramics, polymers and combinations thereof.

* * * * *